United States Patent

Yamashita et al.

Patent Number: 5,965,604
Date of Patent: Oct. 12, 1999

[54] CHROLACTOMYCIN COMPOUND

[75] Inventors: Yoshinori Yamashita; Ryuichiro Nakai; Tamio Mizukami; Shingo Kakita; Shigeru Chiba, all of Machida; Shiro Akinaga, Sunto-gun, all of Japan

[73] Assignee: Kyowa Hakko Kogyo Co., Ltd., Tokyo, Japan

[21] Appl. No.: 09/215,468

[22] Filed: Dec. 17, 1998

[30] Foreign Application Priority Data

Dec. 22, 1997 [JP] Japan ................................. 9-352541

[51] Int. Cl.$^6$ .......................... A01N 43/08; A01N 43/02; C12P 17/08; C07D 307/77
[52] U.S. Cl. ........................ 514/450; 435/119; 435/124; 435/253.5; 435/886; 549/297; 549/298; 549/299; 549/300
[58] Field of Search ..................... 549/300, 298, 549/299, 297; 514/450; 435/886, 119, 253.5, 124

[56] References Cited

FOREIGN PATENT DOCUMENTS

| 62-175493 | 8/1987 | Japan . |
| 63-48284 | 2/1988 | Japan . |
| 64-19079 | 1/1989 | Japan . |

OTHER PUBLICATIONS

The Journal of Antibiotics, Nov. 1987, vol. XL No. 11, pp. 1475–1482.
The Journal of Antibiotics, Nov. 1987, vol. XL No. 11, pp. 1483–1489.
The Journal of Antibiotics, Aug. 1989, vol. XLII No. 8, pp. 1321–1323.

*Primary Examiner*—Herbert J. Lilling
*Attorney, Agent, or Firm*—Fitzpatrick, Cella, Harper & Scinto

[57] ABSTRACT

The present invention relates to chrolactomycin compound represented by the following formula (I):

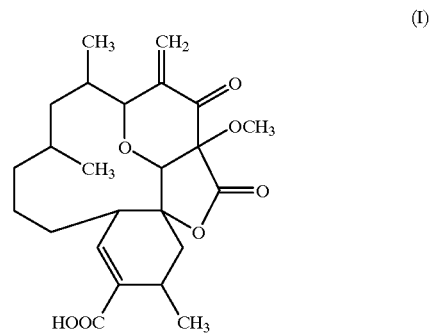

or pharmaceutically acceptable salts thereof having antibacterial and antitumor activities.

7 Claims, No Drawings

CHROLACTOMYCIN COMPOUND

BACKGROUND

1. Field of the Invention

The present invention relates to a chrolactomycin compound or pharmaceutically acceptable salts thereof which have antibacterial and antitumor activities.

2. Brief Description of the Background Art

Okilactomycin represented by the following formula (II):

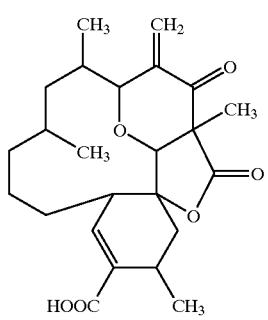

(II)

is reported [Journal of Antibiotics, 40, 1475–1482 (1987)].

SUMMARY OF THE INVENTION

An object of the present invention is to provide a chrolactomycin compound having excellent antibacterial and antitumor activities.

The present invention provides a chrolactomycin compound represented by the following formula (I):

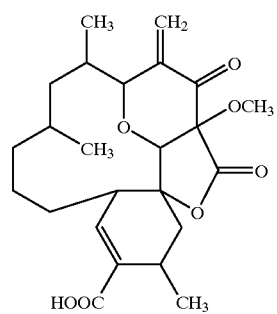

(I)

and pharmaceutically acceptable salts thereof having antibacterial and antitumor activities.

The present invention also relates to a pharmaceutical composition comprising a pharmaceutically acceptable carrier and an effective amount of the chrolactomycin compound defined above as an active ingredient.

The present invention also relates to a method for treating tumor and bacterial disease, which comprises administering an effective amount of the chrolactomycin compound or the pharmaceutically acceptable salt thereof defined above.

The present invention also relates to a process for producing the chrolactomycin compound defined above, comprising culturing a microorganism capable of producing said compound in a medium, and isolating said compound from the culture.

DETAILED DESCRIPTION OF THE INVENTION

The physicochemical properties of the chrolactomycin compound are shown below.

The data were obtained by using the following instruments.

Melting point: Yanagimoto Seisakusho K. K., Micromelting point measuring apparatus Optical rotation: Nippon Bunko Kogyo Co., Ltd., DIP-370 Digital polarimeter FAB MS spectrum and high resolution FAB MS spectrum: JEOL LTD., JMS HX/HX-110A Mass spectrometer UV absorption spectrum: Shimadzu Corporation, UV-2200 Ultraviolet spectrophotometer IR absorption spectrum: JEOL LTD., JIR RFX3001 Infrared spectrometer NMR spectrum: JEOL LTD., JNM-α400 Nuclear magnetic resonance spectrometer Bruker, DMX500 Nuclear magnetic resonance spectrometer

PHYSICOCHEMICAL PROPERTIES OF CHROLACTOMYCIN

Color and form of the substance: white powder

Melting point: 130 to 131° C.

Optical rotation: $[a]_D^{28.5}=-7.75°$ (c=0.45, $CH_3OH$)

Molecular formula: $C_{24}H_{32}O_7$

FAB MS spectrum: m/z 433 $[M+H]^+$, 431 $[M-]^+$

High resolution FAB MS spectrum:

Found: 431.2087

Theoretical: 431.2069 (as $C_{24}H_{31}O_7$)

UV absorption spectrum (2.25 mg/40 ml, $CH_3OH$):

$\lambda_{max}$ 209.8 nm ($\epsilon$4,738)

IR absorption spectrum (KBr): $v_{max}$ 3800–2400, 3410, 2954, 2929, 2866, 1793, 1712, 1689, 1641, 1626, 1458, 1255, 1186, 1178, 1113, 1074, 966 cm$^{-1}$ $^1$H-NMR spectrum: $\delta(CDCl_3)$ 0.89(3H, d, J=6.8 Hz), 0.94(1H, m), 1.03(1H, m), 1.08(3H, d, J=6.6 Hz), 1.12(3H, d, J=6.8 Hz), 1.21(1H, m), 1.25(1H, m), 1.34(1H, ddd, J=2.0, 6.7, 14.9 Hz), 1.55(1H, dd, J=9.6, 14.3 Hz), 1.61 (1H, m), 1.62(2H, m), 1.76(1H, dd, J=10.5, 14.9 Hz), 1.79(1H, m), 1.95(1H, m), 2.34(1H, m), 2.71(1H, m), 3.60(3H, s), 4.26(1H, br.d, J=9.8 Hz), 4.53(1H, s), 5.67(1H, d, J=1.7 Hz), 6.41(1H, d, J=1.0 Hz), 6.83(1H, dd, J=1.8, 6.0 Hz) ppm $^{13}$C-NMRspectrum: $\delta(CDCl_3)$ 20.1 (q), 20.5(q), 23.6(q), 23.8(t), 27.2(d), 30.4(d), 32.1(t), 34.3 (t), 34.5(d), 37.6(t), 42.7(d), 45.1(t), 54.6(q), 78.6(s), 82.1 (d), 83.4(s), 84.0(d), 121.1(t), 132.9(s), 140.9(d), 143.7(s), 168.9(s), 171.0(s), 190.1(s) ppm Solubility: Soluble in methanol, acetone, ethyl acetate, chloroform and dimethylsulfoxide (DMSO) and sparingly soluble in hexane.

Color reaction: Positive to iodine reagent, sulfuric acid/ethanol reagent, phosphomolybdate/cerium sulfate reagent, and orcinol sulfate.

Thin-layer chromatography: Rf value; 0.41

Thin layer; silica gel TLC (Merck & Co., Inc.)

Developing solvent; chloroform:methanol (19:1, v/v)

The process for producing a chrolactomycin compound is described below.

A chrolactomycin compound can be obtained by culturing in a medium a microorganism belonging to the genus Streptomyces and having the ability to produce a chrolactomycin compound, allowing a chrolactomycin compound to accumulate in the culture, and recovering the chrolactomycin compound from the culture.

As the strains having the ability to produce a chrolactomycin compound, any strains which belong to the genus Streptomyces and have the ability to produce a chrolactomycin compound can be used. In addition, any mutants of such strains which are obtained by various artificial mutation methods such as UV irradiation, X-ray irradiation and treatment with mutagens or by spontaneous mutation may also be used in the present invention, insofar as they have the ability to produce a chrolactomycin compound. A typical example of a suitable stain is Streptomyces sp. 569N-3 strain.

The typical strain (569N-3) capable of producing the compound of the present invention has been isolated from the soil sample, and has the following mycological properties:

1. Morphological Characteristics
   1) Hyphae
   Formation of aerial hyphae: observed
   Fragmentation and motility of aerial hyphae: not observed
   Fragmentation and motility of substrate hyphae: not observed
   2) Spores
   Formation and location of spores: formed on aerial hyphae
   Formation and location of sporangia: not observed
   Number of spores in chain formed at the end of the sporophore: 10 or more
   Form of spore chains: curved or spiral
   Characteristics of spores
   Surface: smooth
   Form and size: Rods, about 0.5 to 0.7 $\mu$m×0.7 to 0.8 $\mu$m
   Motility and flagellum: not observed
   3) Others
   Chlamydospores: not observed
   Synnemata: not observed
   Pseudosporangia: not observed
   Branching mode of hyphae: simple branching
2. Cultural Characteristics
   The 569N-3 strain grows weakly or vigorously on synthetic and natural media which are generally used. The color of the substrate hyphae is ocher to dark brown. Formation of soluble brown pigment was observed on some of the culture media.
   The cultural characteristics such as growth and color after culturing at 28° C. for 14 days are shown below. The color names are given according to Color Harmony Manual (Container Corporation of America, 4$^{th}$ edition, 1958).
   1) Sucrose-nitrate agar medium
      Growth: normal
      Color of substrate hyphae: white (a)
      Formation and color of aerial hyphae: normal, white (a)
      Soluble pigment: none
   2) Glucose-asparagine agar medium
      Growth: vigorous
      Color of substrate hyphae: light beige (3ec) to beige brown (3ig)
      Formation and color of aerial hyphae: none
      Soluble pigment: none
   3) Glycerin-asparagine agar medium
      Growth: weak
      Color of substrate hyphae: light olive gray (1$_{1/2}$ge)
      Formation and color of aerial hyphae: none
      Soluble pigment: none
   4) Starch-inorganic salt agar medium
      Growth: vigorous
      Color of substrate hyphae: camel (3ie) to foun (4ig)
      Formation and color of aerial hyphae: normal, white (a) to pussy willow (5dc)
      Soluble pigment: none
   5) Tyrosine agar medium
      Growth: vigorous
      Color of substrate hyphae: beaver (3li) to chocolate (4nl)
      Formation and color of aerial hyphae: normal, pussy willow (5dc) to lead gray (5ih)
      Soluble pigment: formed (brown)
   6) Nutrient agar medium
      Growth: weak
      Color of substrate hyphae: light citron gray (1ec) to citron (1gc)
      Formation and color of aerial hyphae: none
      Soluble pigment: none
   7) Yeast-malt agar medium
      Growth: vigorous
      Color of substrate hyphae: light brown (3lg)
      Formation and color of aerial hyphae: none
      Soluble pigment: slightly formed (brown)
   8) Oatmeal agar medium
      Growth: vigorous
      Color of substrate hyphae: light brown (3lg) to light spice brown (4lg)
      Formation and color of aerial hyphae: normal, white (a) to pussy willow (5dc)
      Soluble pigment: formed (brown)
3. Physiological Characteristics
   The physiological characteristics of 569N-3 strain are shown below. The result of 1) was obtained after 14 days of culturing, and the results of 2)–6) were obtained after 2 weeks of culturing at 28° C.
   1) Growth temperature range: 10.8 to 33.0° C.
   2) Gelatin liquefaction: positive
   3) Starch hydrolysis: positive
   4) Coagulation and peptonization of skim milk powder: negative
   5) Production of melanin-like pigment
      (1) Peptone-yeast-iron agar medium: negative
      (2) Tyrosine agar medium: positive
   6) Assimilability of carbon sources
      The basal medium used was a Pridham Gottlieb agar medium. In the following, "+" indicates that the strain utilized the carbon source, "–" indicates that the strain did not utilize the carbon source, and "W" indicates that it is not clear whether the strain utilized the carbon source.
      L-arabinose: –
      D-xylose: –
      D-glucose: +
      Sucrose: –
      Raffinose: +
      D-fructose: W
      Rhamnose: +
      Inositol: –
      D-mannitol: –
4. Chemotaxonomic Characteristics
   1) Optical isomer of diaminopimelic acid in the strain: LL form 2) Major quinone components of cellular lipid: MK-9 (H6), MK-9 (H8)

The strain is classified into the genus Streptomyces among actinomycetes in view of its characteristics: that spore chains are formed on the aerial hyphae, that it belongs to the Type I cell wall group (LL-diaminopimelic acid); and that the major quinone components are a 3-saturated type menaquinone 9 [MK-9 (H6)] and a 4-saturated type menaquinone 9 [MK-9 (H8)].

The strain was named Streptomyces sp. 569N-3 and was deposited with the National Institute of Bioscience and Human-Technology, Agency of Industrial Science and Technology (Higashi 1-1-3, Tsukuba City, Ibaraki Pref., JP) on Oct. 30, 1997 with the accession number FERM BP-6158, under the Budapest Treaty.

For culturing the chrolactomycin-compound-producing strains of the present invention, conventional methods for culturing actinomycetes are generally employed. As the medium, either a synthetic medium or a natural medium may be used insofar as it appropriately contains carbon sources, nitrogen sources, inorganic substances, and the like which can be assimilated by the strains employed.

Examples of the carbon sources include glucose, starch, dextrin, mannose, fructose, sucrose, lactose, xylose, arabinose, mannitol, molasses and the like which are used singly or in combination. Depending on the assimilation ability of the strains, hydrocarbons, alcohols, organic acids and the like can also be used.

Examples of the nitrogen sources include ammonium chloride, ammonium nitrate, ammonium sulfate, sodium nitrate, urea, peptone, meat extract, yeast extract, dry yeast, corn steep liquor(CSL), soybean meal(SBM), casamino acid and the like which are used singly or in combination.

Besides, inorganic salts such as sodium chloride, potassium chloride, magnesium sulfate, calcium carbonate, potassium dihydrogenphosphate, magnesium phosphate.$8H_2O$, ferrous sulfate, calcium chloride, manganese sulfate, zinc sulfate and copper sulfate may be added, if necessary. Further, trace ingredients that promote the growth of the strain used or the production of the chrolactomycin compound may be added to the medium, if necessary.

The culturing method is preferably a liquid culture method, the more preferably a submerged stirring culture method. Culturing is carried out at 16 to 37° C., preferably 25 to 32° C., and at pH 4 to 10, preferably pH 6 to 8. For pH adjustment of the medium, aqueous ammonia, an ammonium carbonate solution or the like is used. Generally, culturing is completed in 1 to 7 days, and a chrolactomycin compound is produced and accumulated in the culture broth and in the microbial cells. It is preferable to discontinue culturing when the amount of the product accumulated in the culture reaches the maximum.

For the isolation and purification of a chrolactomycin compound from the culture, an ordinary method for isolating a microbial metabolite from the culture can be utilized. For example, the culture is separated by filtration into a culture filtrate and microbial cells, and the microbial cells are extracted with a solvent such as chloroform, acetone, methanol or the like. Then, the extract is mixed with the culture filtrate, and the resultant mixture is passed through a column of polystyrene adsorbent such as Diaion HP-20 (Mitsubishi Chemical Corporation) to adsorb the active substance, followed by elution with a solvent such as methanol or acetone. The eluate is concentrated, and the concentrate is subjected to column chromatography on octadecyl group-bound silica gel (ODS), high performance liquid chromatography (HPLC), or column chromatography on silica gel, to give a chrolactomycin compound. During the procedures of culturing, isolation and purification, a chrolactomycin compound can be detected by using thin layer chromatography (TLC), and then an iodine reagent.

The pharmaceutically acceptable salts of a chrolactomycin compound include pharmaceutically acceptable metal salts, ammonium salts, organic amine addition salts, and amino acid addition salts. The metal salts include alkali metal salts such as lithium salt, sodium salt, and potassium salt, alkaline earth metal salts such as magnesium salt, and calcium salt, aluminum salt, zinc salt, etc.; the ammonium salts include ammonium, tetramethylammonium, etc.; the organic amine addition salts include salts with morpholine, piperidine or the like; and the amino acid addition salts include salts with glycine, phenylalanine, aspartic acid, glutamic acid, lysine or the like.

When the desired product is a salt of a chrolactomycin compound and the compound actually obtained is such a salt, it can be directly purified and recovered as a product. When the compound obtained is a free compound, it can be converted into its salt by dissolving or suspending it in a suitable solvent and adding a base thereto.

A chrolactomycin compound may exist in the form of various isomers such as tautomers and structural isomers, and the present invention covers all possible isomers including these isomers and mixtures thereof.

A chrolactomycin compound and pharmaceutically acceptable salts thereof may exist in the form of adducts with water or various kinds of solvents, which are also within the scope of the present invention.

The biological activity of the chrolactomycin compound is described below by Test Examples.

TEST EXAMPLE 1

Antibacterial Activity Against Bacteria:

The antibacterial activity of a chrolactomycin compound against bacteria was examined.

The antibacterial activity was determined by an agar dilution method using a medium (pH 7) composed of 3 g/L Bacto-trypton (Difco), 3 g/L meat extract, 1 g/L yeast extract, 1 g/L glucose and 16 g/L agar. The antibacterial activity was shown by minimum inhibitory concentration (MIC).

The result is shown in Table 1.

TABLE 1

| Test Microorganisms | MIC ($\mu$g/ml) |
| --- | --- |
| Staphylococcus aureus ATCC6538P | 5.2 |
| Enterococcus hirae ATCC10541 | 10.4 |
| Bacillus subtilis No. 10707 | 5.2 |

TEST EXAMPLE 2

Growth Inhibition Against Human Mammary Cancer MCF-7, Human Bladder Cancer T24, Human Epidermal Cancer A431 and Human Renal Cancer ACHN Cells:

Respective cells were dispensed into a 96-well microtiter plate (Nunc#167008) in $1\times10^3$ cells/well portions in the case of MCF-7 and T24 or in $1.5\times10^3$ cells/well portions in the case of A431 and ACHN and cultured at 37° C. for 24 hours in a 5% $CO_2$ incubator. Thereafter, a 30 mM solution of a chrolactomycin compound was diluted stepwise by 3-fold, and the resulting solution was added to each well in an amount of 50 $\mu$l. The final concentration of each solution was 100 $\mu$M at the maximum at this stage. They were cultured again at 37° C. for 72 hours in the 5% $CO_2$ incubator. Five hours before the end of the culturing, MTT [3-(4-dimethylthiazol-2-yl)-2,5-diphenyltetrazolium bromide, Sigma] which had been dissolved in the culture medium to a final concentration of 1 mg/ml was dispensed into the plate in 50 μl/well portions. After completion of the culturing, DMSO was dispensed in 150 μl/well portions, and the resulting mixture was stirred vigorously with a plate mixer to completely dissolve MTT-formazan crystals. The absorbance at 550 nm was measured by a micro-plate spectrophotometer M-SPmax 250 (Wako Pure Chemical Industries, Ltd.). The cell growth inhibiting activity was shown by the 50% inhibitory concentration ($IC_{50}$).

The result is shown in Table 2.

TABLE 2

| Compound | $IC_{50}$ (μM) | | | |
| --- | --- | --- | --- | --- |
|  | MCF-7 | T24 | A431 | ACHN |
| Chrolactomycin | 0.69 | 0.45 | 1.6 | 1.2 |

Certain embodiments of the invention are shown in the following Example.

EXAMPLE

Example 1
Production of Chrolactomycin by Streptomyces sp. 569N-3 strain:

The first and second seed culture media used were those (pH 7.2) composed of 10 g/L glucose, 10 g/L soluble starch, 5 g/L Bacto-trypton, 3 g/L meat extract, 5 g/L yeast extract, and 0.5 g/L magnesium phosphate,$8H_2O$.

One loopful of the strain was inoculated into 10 ml of the first seed culture medium in each of two 70-ml test tubes and cultured at 28° C. for 216hours under shaking. The resulting first seed culture (20 ml) was inoculated in 6.25 ml portions into 125 ml of the second seed medium in each of two 2-L Erlenmeyer flasks and cultured at 28° C. for 48 hours under shaking.

The resulting second seed culture was inoculated in 125 ml portions into 2.5 L of a main fermentation medium (total amount of the medium: 5 L) in each of two 5-L tanks and cultured at 28° C. for 140 hours with aeration under stirring (rotation: 500 rpm; aeration: 2.5 L/min.). The main fermentation medium used was a medium (pH 7.0) composed of 40 g/L soluble starch, 10 g/L SBM, 5 g/L CSL, 5 g/L dry yeast, 5 g/L potassium dihydrogenphosphate, 0.01 g/L zinc sulfates.$7H_2O$, 0.001 g/L cobalt chloride.$6H_2O$, 0.001 g/L nickel sulfate, and 0.5 g/L magnesium phosphate.$8H_2O$.

To the resulting fermentation culture (4 L) was added a filter aid (Radiolite #600, Showa Kagaku Kogyo Co., Ltd.) at a concentration of 10%, followed by filtration in a centrifuge. To the strain which was thus separated from the culture filtrate was added 750 ml of methanol, and the mixture was sufficiently stirred and extracted, and filtered again under suction in the centrifuge. The resulting methanol extract was mixed with the culture filtrate, and water was further added thereto to give 4 L of a solution. This was passed through a column packed with 220 ml of Diaion HP-20 to adsorb the active components. Impurities were eluted with 700 ml of a 80% aqueous methanol solution, and then the active components were eluted with 700 ml of methanol. The active fraction was concentrated to dryness under reduced pressure to give a brown oily substance. This oily substance was dissolved in a small amount of methanol and passed through a column packed with 100 ml of Diaion HP-20SS to adsorb the active components. Impurities were eluted with 300 ml of a 60% aqueous acetonitrile solution, and then the active components were eluted with 300 ml of a 70% aqueous acetonitrile solution. The active fraction was concentrated to dryness under reduced pressure to give a brown oily substance. This oily substance was dissolved in a small amount of chloroform, applied to a silica gel column (Wako Gel C-200, Wako Pure Chemical Industries, Ltd.) and developed with a chloroform-methanol mixture. Impurities were eluted with a chloroform/methanol (100:1, v/v) mixture, and then the active components were eluted with a chloroform/methanol (50:1, v/v) mixture. The active fraction was concentrated to dryness under reduced pressure to give a brown oily substance. This oily substance was dissolved again in a small amount of chloroform, applied to a silica gel column (Lichroprep Si 60, Merck & Co., Inc.) and developed with an ethyl acetate/methanol mixture. Impurities were eluted with ethyl acetate, and then the active fraction was eluted with methanol. This was concentrated and subjected to preparative high performance liquid chromatography (HPLC) under the following conditions to give the active fraction. The active components were extracted with ethyl acetate and concentrated to dryness to give 23.2 mg of chrolactomycin.

HPLC Conditions:
Column: ODS-HG-5 (Develosil Ltd.)
Flow rate: 10 ml/min.
Detection: 230 nm
Eluent: acetonitrile/10 mM potassium phosphate buffer (pH 5.9) (a linear gradient of from 2:8 to 7:3 (v/v), 0 to 50 minutes)
Retention time: 41 minutes As described above, a chrolactomycin compound having antibacterial and antitumor activities and pharmaceutically acceptable salts thereof can be provided according to the present invention.

What is claimed is:

1. A chrolactomycin compound represented by the following formula (I):

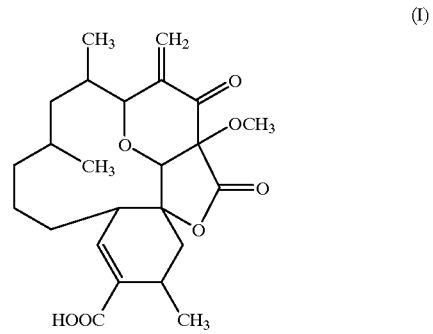

or a pharmaceutically acceptable salt thereof.

2. A pharmaceutical composition comprising a pharmaceutically acceptable carrier and an effective amount of the chrolactomycin compound according to claim 1.

3. A method for treating tumor, which comprises administering the chrolactomycin compound or the pharmaceutically acceptable salt thereof according to claim 1.

4. A method for treating bacterial disease, which comprises administering the chrolactomycin compound or the pharmaceutically acceptable salt thereof according to claim 1.

5. A process for producing the chrolactomycin compound according to claim 1, comprising culturing a microorganism capable of producing said compound in a medium, and isolating said compound from the culture.

6. The process for producing according to claim 5 wherein the microorganism belongs to Streptomyces.

7. The process for producing according to claim 5 wherein the microorganism is Streptomyces sp. 569N-3 strain (FERM BP-6158).

* * * * *